United States Patent
Cevey et al.

(10) Patent No.: US 6,884,070 B2
(45) Date of Patent: Apr. 26, 2005

(54) POWDER RESERVOIR FOR A DENTAL ABRASIVE SPRAYER

(75) Inventors: Julien Cevey, Crans-Pres-Celigny (CH); Lutz Beerstecher, Borex (CH)

(73) Assignee: Ferton Holding S.A. (CH)

( * ) Notice: Subject to any disclaimer, the term of this patent is extended or adjusted under 35 U.S.C. 154(b) by 143 days.

(21) Appl. No.: 10/104,688

(22) Filed: Mar. 21, 2002

(65) Prior Publication Data

US 2002/0137005 A1 Sep. 26, 2002

(30) Foreign Application Priority Data

Mar. 23, 2001 (DE) ........................................ 101 14 325

(51) Int. Cl.[7] .................................................. A61C 3/02
(52) U.S. Cl. ........................................................ 433/88
(58) Field of Search .............................. 433/88; 451/90, 451/79, 100; 239/142, 311; 406/75

(56) References Cited

U.S. PATENT DOCUMENTS

| | | | | |
|---|---|---|---|---|
| 1,664,369 A | | 3/1928 | Maurer | 433/88 |
| 2,597,434 A | * | 5/1952 | Bishop et al. | 451/3 |
| 2,696,049 A | | 12/1954 | Black | 433/88 |
| 4,482,322 A | | 11/1984 | Hain et al. | 433/88 |
| 4,492,575 A | | 1/1985 | Mabille | 433/88 |
| 5,330,354 A | * | 7/1994 | Gallant | 433/88 |
| 5,618,177 A | * | 4/1997 | Abbott | 433/88 |
| 6,083,001 A | | 7/2000 | Deardon et al. | 433/88 |
| 6,179,614 B1 | | 1/2001 | Elrod et al. | 433/88 |

FOREIGN PATENT DOCUMENTS

| DE | 32 12 207 A1 | 10/1983 |
|---|---|---|
| DE | 295 08 873 U1 | 10/1996 |

* cited by examiner

Primary Examiner—John J Wilson
(74) Attorney, Agent, or Firm—Ostrolenk, Faber, Gerb & Soffen, LLP

(57) ABSTRACT

A powder reservoir for a dental abrasive blasting apparatus is provided with a discharge valve having a closure body that comprises associated driving means for moving a closure body with a pulsed frequency alternately between a closing position and an opening position of an associated discharge opening of the powder reservoir for discharging the powder into a mixing chamber which is passed by a supply line for compressed air for supplying a handpiece with a mixture of compressed air and abrasive powder particles.

19 Claims, 4 Drawing Sheets

POWDER RESERVOIR FOR A DENTAL ABRASIVE SPRAYER

FIELD OF THE INVENTION

The present invention relates to a powder reservoir for a dental abrasive blasting apparatus which is connected with a handpiece having a nozzle arrangement at a tip portion for discharging a working jet of a mixture of compressed air and abrasive powder particles which is supplied from a mixing chamber that is arranged below a discharge opening of the powder reservoir.

BACKGROUND OF THE INVENTION

A prior art powder reservoir of the kind as herein referred is described in U.S. Pat. No. 1,664,369. For obtaining a measured out admixture of the powder particles a feed screw driven by a motor is arranged in a cylindrically formed mixing chamber for feeding the powder particles that are discharged into the mixing chamber at the one end of the feed screw to an exit which is provided at an opposite end of the feed screw. At this opposite end compressed air is supplied into the mixing chamber for taking up the powder particles and transporting the mixture further along a connecting line with the handpiece.

The U.S. Pat. No. 2,696,049 discloses a mesh screen which is arranged for closing the discharge opening of a powder reservoir and for determining the dosage of the powder particles that are supplied via the screen to the mixing chamber for being mixed with a gaseous stream that is passed through the mixing chamber along the underside of the mesh screen. For supporting the discharge of the powder particles and for also avoiding any clogging of the screen the powder reservoir is arranged on a vibratory plate which is electromagnetically driven for oscillating the powder reservoir horizontally and vertically whereby the oscillations of the powder reservoir also contribute indirectly to move the powder particles towards the screen which closes the discharge opening of the powder reservoir.

The U.S. Pat. No. 4,482,322 discloses for same purposes an electromagnetically driven vibration device which supports a powder reservoir having a discharge opening which is normally closed by a diaphragm. The diaphragm is fixed along a rim portion and biased towards its closing position by a compression spring for supporting a pneumatic pressure compensation which is regulated for a mixing chamber which is provided underneath of discharge opening of the powder reservoir. The diaphragm separates the mixing chamber against a pressure compensation chamber and is transferred to a permanent opening position as soon as a pressure release via a branch line of a passage line for compressed air is regulated by means of a venting valve. In the opening position of the diaphragm the discharge of the powder particles from the powder reservoir will primarily be supported by the stream of compressed air which is directed over the upper surface of the diaphragm and stimulating a vortex motion inside of the mixing chamber The mixing chamber is designed by structural features as a specific vortex chamber into which the powder particles are discharged with the additional support of the vibration device which is switched-on in the opening position of the diaphragm.

SUMMARY OF THE INVENTION

An object of the present invention is to provide a powder reservoir for a dental abrasive blasting apparatus whereby a more precise dosage of the powder particles as admixed to the stream of compressed air when passed through the mixing chamber will be available without any support of a vibration system or other supplementary measures.

The present invention accordingly provides a powder reservoir for a dental abrasive blasting apparatus which is characterised by the features as outlined in the claims.

A powder reservoir for a dental abrasive blasting apparatus in accordance with the present invention therefore simply includes a driving means which is directly associated with a closure body of a discharge valve that is biased towards a closing position of the discharge opening of the powder reservoir for normally blocking discharge of powder particles into the mixing chamber. The driving means is arranged for moving the closure body of the discharge valve into pulsed opening positions alternately with respect to closing positions so that the powder particles will be discharged from the powder reservoir in a pulsed sequence at a pulse frequency which is controlled for example in a range between 0.5 and 100 Hz at a pulse width between 0 and 100%. With such a pulsed actuation of the closure body of the discharge valve a very precise dosage may be obtained for the powder particles as admixed to the stream of compressed air whereby this dosage could as well be simply varied by varying the pulse frequency of the driving means. With such a pulsed activation of the closure body of the discharge valve motion is also transmitted to the powder particles which during dental treatment are still contained in the powder reservoir so that these remaining powder particles will be freed more easily for their discharge into the mixing chamber.

Other objects, features and advantages of the present invention will become apparent from reading the following description of a preferred embodiment of a powder reservoir according to the present invention.

DETAILED DESCRIPTION

Figure 1:
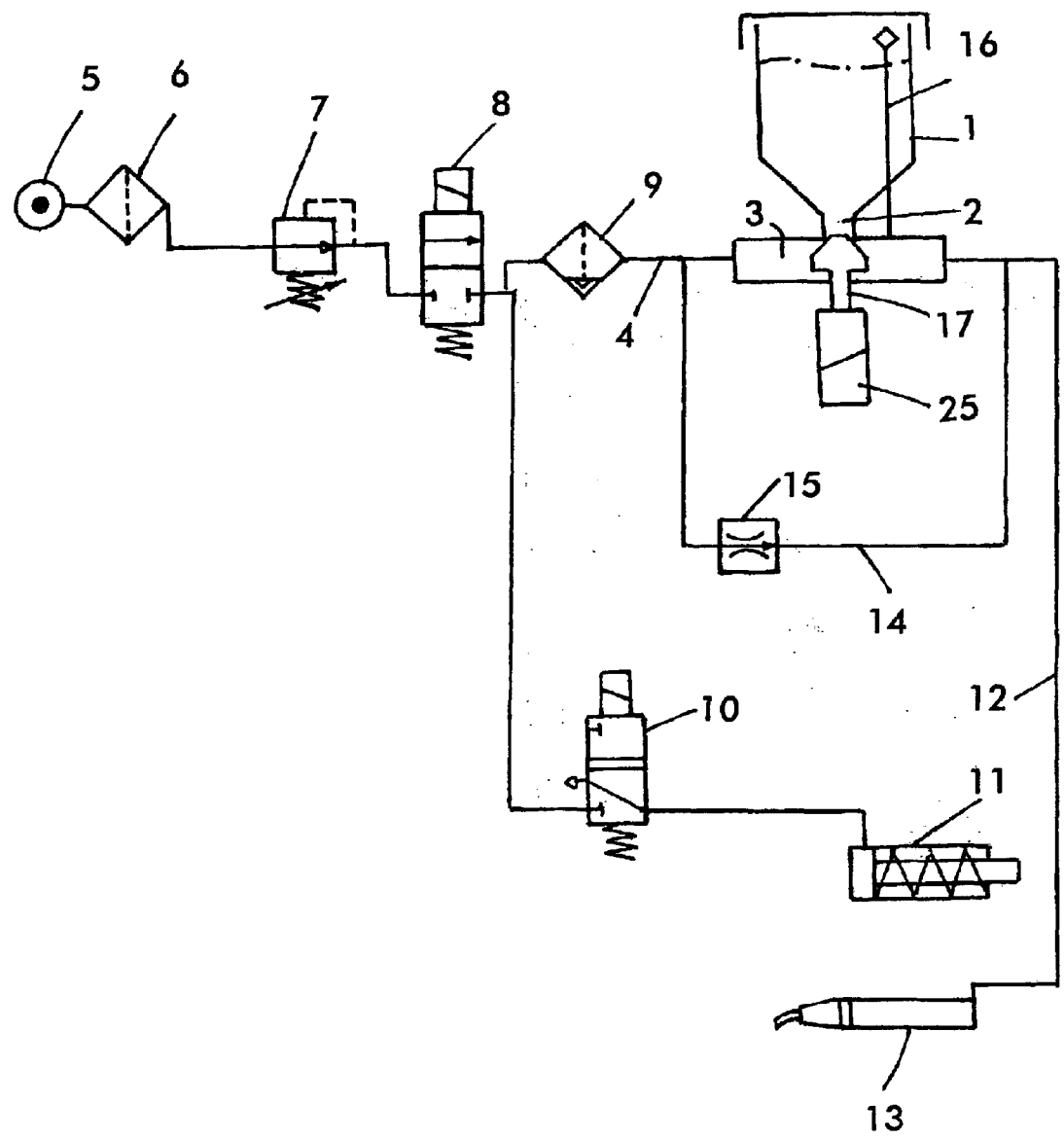
FIG. 1 is a diagrammatic view of a dental abrasive blasting apparatus incorporating a powder reservoir according to the present invention.

A dental abrasive blasting apparatus which uses a powder reservoir according to the present invention is basically designed in the same manner as the dental apparatus according to the U.S. Pat. No. 4,492,575 to which reference may therefore be made for further details of the following description.

The dental abrasive powder which is usually used with such an apparatus is normally contained in a powder reservoir 1 having a discharge opening 2 at its bottom for discharging the powder into a mixing chamber 3 which is arranged below the discharge opening. A stream of compressed air is passed through an associated pressure line 4 which connects to a pressure source 5. Downstream of this pressure source 5 an air filter 6, a pressure regulator 7, a directional control valve 8 and a further air filter 9 are arranged in series in the pressure line 4 which also connects via a branch line to a further directional control valve 10 which controls a pneumatic pinch valve 11. The pinch valve 11 is arranged for blocking supply of an air-powder-mixture via a connecting line 12 of the mixing chamber 3 to an associated handpiece 13 which could further be connected with an associated supply line for water. A further branch line 14 of the pressure line 4 is provided with a flow nozzle 15, and a still further branch line 16 connects to the powder reservoir 1 for ending at a position above the level of the powder which is contained in the powder reservoir.

Figure 2:
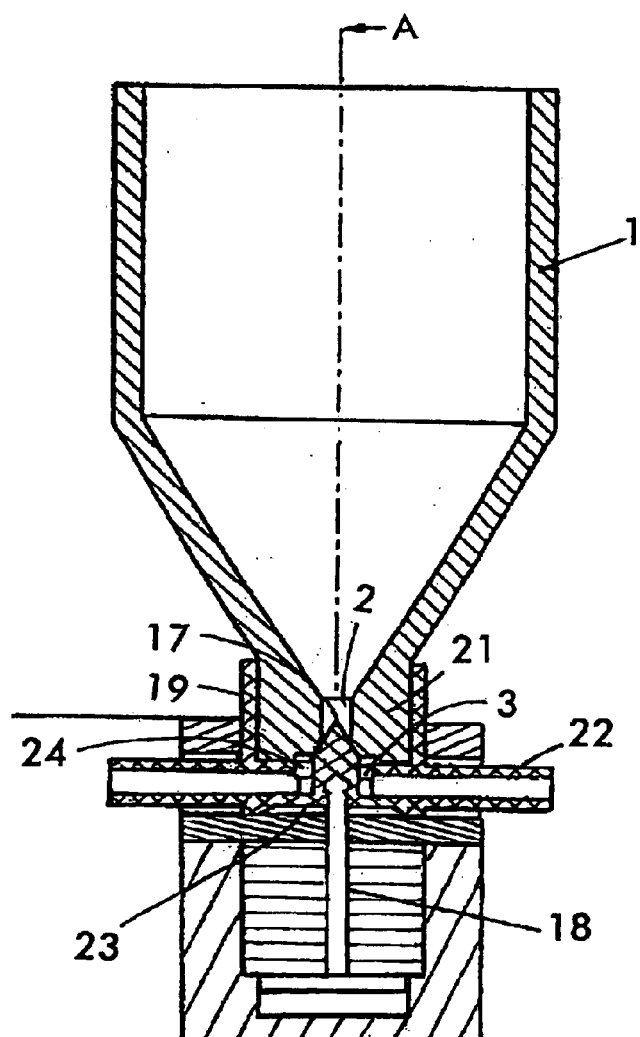
FIG. 2 is a sectional view of powder reservoir in accordance with the present invention and incorporating a first embodiment of a discharge valve which is arranged on a discharge opening of the powder reservoir.

For providing discharge of the powder from the powder reservoir 1 into the mixing chamber 3 and its admixture the air stream which is passed through the mixing chamber the discharge is controlled by a discharge valve having a closure member 17 which in the embodiment of FIG. 2 is designed as a substantially needle-shaped member that projects towards the discharge opening 2 of the powder reservoir. FIG. 2 illustrates the closing position of this needle-shaped closure member 17 which is pushed into this closing position by an associated lifting magnet 18 of an electromagnetic driving means. The electromagnetic driving means is controlled such as to move the closure member 17 of the discharge valve into a pulsed opening position alternately with respect to its closing position whereby the powder will be discharged from the powder reservoir 1 in the opening position of the needle-shaped closure member 17 at a rate which is related to the pulse frequency of the electromagnetic driving means and its lifting magnet. The pulse frequency therefore determines any desired dosage for the admixture of the powder particles to the compressed air which is passed through the mixing chamber 3 so that with any variation of this pulse frequency the dosage of the powder particles will be correspondingly adapted to any newly regulated pulse frequency. The pulse frequency of the driving means could thusly be controlled for example in a range between 0.5 and 100 Hz at a pulse width between 0 and 100% whereby it of course should be understood as well that a particular dosage also depends on the needle-shape of the closure member 17 which therefore is not restricted to the particular design illustrated in the drawing. By actuating the closure member of the discharge valve with such a pulse frequency between a closing and an opening position this will also result in transferring a motion into the volume of the powder which is stored in the powder reservoir so that with this transmitted motion the powder particles will be hindered of blocking the discharge opening of the fluid reservoir and therefore maintenance of any desired dosage is as well complemented.

As illustrated in FIG. 2 the needle-shaped valve member 17 forms an integrated part of a valve body 19 which is formed of a rubber-elastic material. The valve body 19 comprises a primary cup-shaped chamber 20 of such a size as to allow a slip-on fixation of the valve body 19 on a lower neck portion 21 which surrounds the discharge opening 2 of the powder reservoir 1. The mixing chamber 3 is on the other hand formed by a secondary chamber of this rubber-elastic valve body 19 and comprises an integrated passage line 22 for passing the compressed air through this secondary chamber. It is to be understood that the supply line 4 for compressed air will be connected to the one end of this passage line 22 and the associated connecting line 12 which connects to the handpiece 13 is connected to the opposite end of the passage line 22. The passage line 22 is provided with an undercut wall portion 23 on which the needle-shaped valve member 17 is formed as an integrated body whereby a passage opening 24 opposite to the undercut wall portion 23 is arranged for accommodating a projection of the needle-shaped valve member 17 towards the discharge opening 2 of the powder reservoir.

Figure 3:
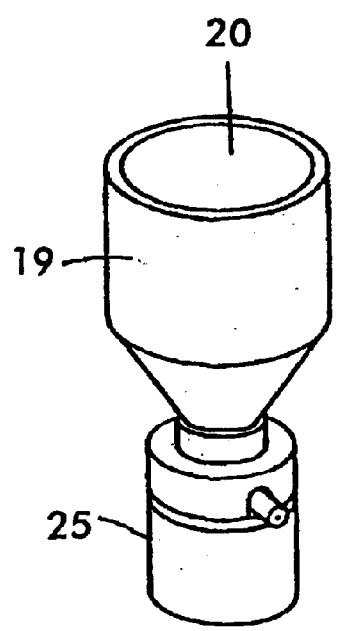
FIG. 3 is perspective illustration of an attach unit incorporating the valve arrangement of FIG. 2 and illustrated to scale.

As illustrated in FIG. 3 the valve body 19 is designed as an attach unit which also comprises an electromagnetic driving means 25 for the lifting magnet 18 so that with such an arrangement the powder reservoir 1 when empty may be easily replaced by a new powder reservoir being filled with a dental powder for use with a dental abrasive blasting apparatus of the kind as diagrammatically illustrated in FIG. 1. As regards a proper control of a pulsed motion of the lifting magnet 18 which is directly connected with the needle-shaped valve member 17 any skilled person will have access to multiple possibilities which will also include a possibility for varying the pulse frequency within the above noted range.

Figure 4:
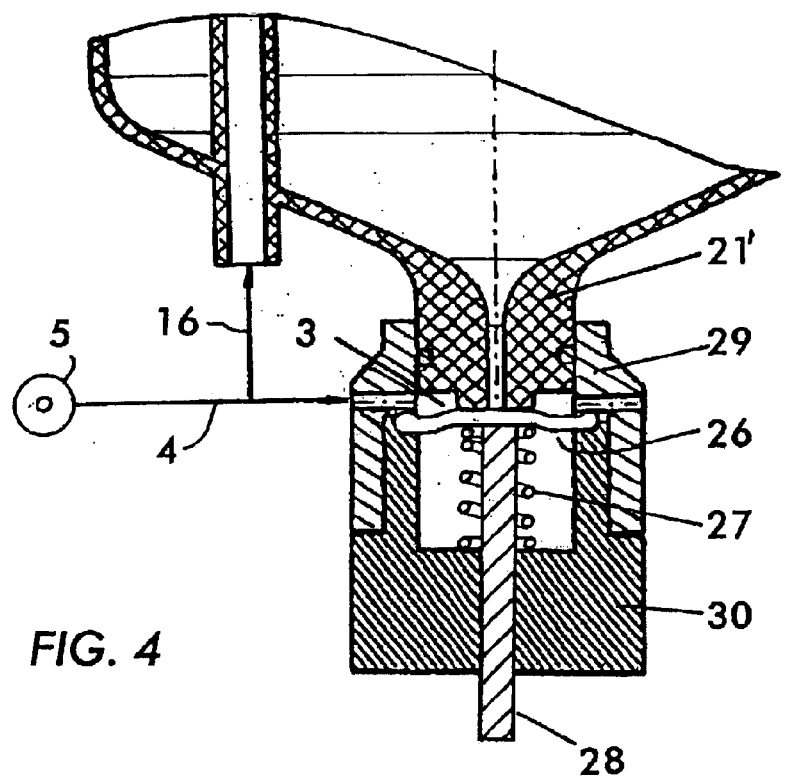
FIG. 4 is a sectional view of a second embodiment of a discharge valve incorporating an electromagnetic driving means as in case of the valve arrangement of FIG. 2.

FIG. 4 illustrates a second embodiment of the discharge valve. A closure body of the discharge valve is formed as a disk-shaped diaphragm 26 which by means of a compression spring 27 is biased towards a closing position of a discharge opening of the powder reservoir. The diaphragm 26 is fixed to a lifting magnet 28 of an electromagnetic driving means to thusly allow as well a pulsed motion of the diaphragm alternately between the closing position as illustrated in FIG. 4 and an opening position in which the powder particles are discharged from the powder reservoir 1' into an associated mixing chamber 3'. The embodiment of FIG. 4 is also designed as an attach unit which comprises two members 29 and 30 that are screw-connected with each other and also with a lower neck portion 21' of the powder reservoir. The diaphragm 26 is fixedly held by its rim portion between the two members 29 and 30 of which the one member 29 is provided with a passage bore for the compressed air as supplied by the associated connecting line 4 of the pressure source 5.

Figure 5:
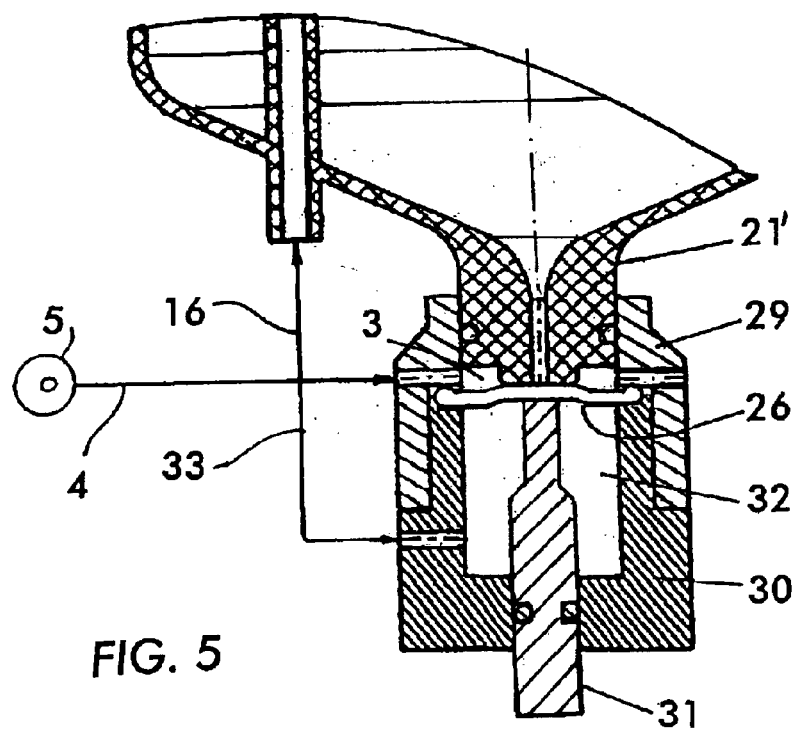
FIG. 5 is a sectional view of a third embodiment of the discharge valve whereby instead of a electromagnetic driving a pneumatic drive is provided for the closure body of the discharge valve.

The embodiment of FIG. 5 is provided with a pneumatic drive means comprising a piston 31 which is fixedly connected with a diaphragm 26' which as in case of the embodiment of FIG. 4 is held by its rim portion between two members 29 and 30 of a corresponding attach unit. A pressure compensation chamber 32 is formed beneath the diaphragm 26' and connected by a branch line 33 with the supply line 4 for compressed air which connects to the mixing chamber 3'. The mixing chamber is provided by the upper space between the diaphragm and the connecting end of the neck portion 21' of the powder reservoir 1' with the one member 29 of the attach unit. The diaphragm 26' could further comprise a needle-shaped valve member as in case of the embodiment of FIG. 2. Since the supply line 4 for compressed air is connected via a branch line 33 with the pressure compensation chamber 32 which is formed by the member 30 beneath the diaphragm 26' a very precise motion of the diaphragm 26' with a pulsed frequency alternately between the closing position as illustrated in FIG. 5 and an opening position will be secured whereby the pneumatic drive means including the piston 31 will be readily available for any skilled person.

Figure 6:
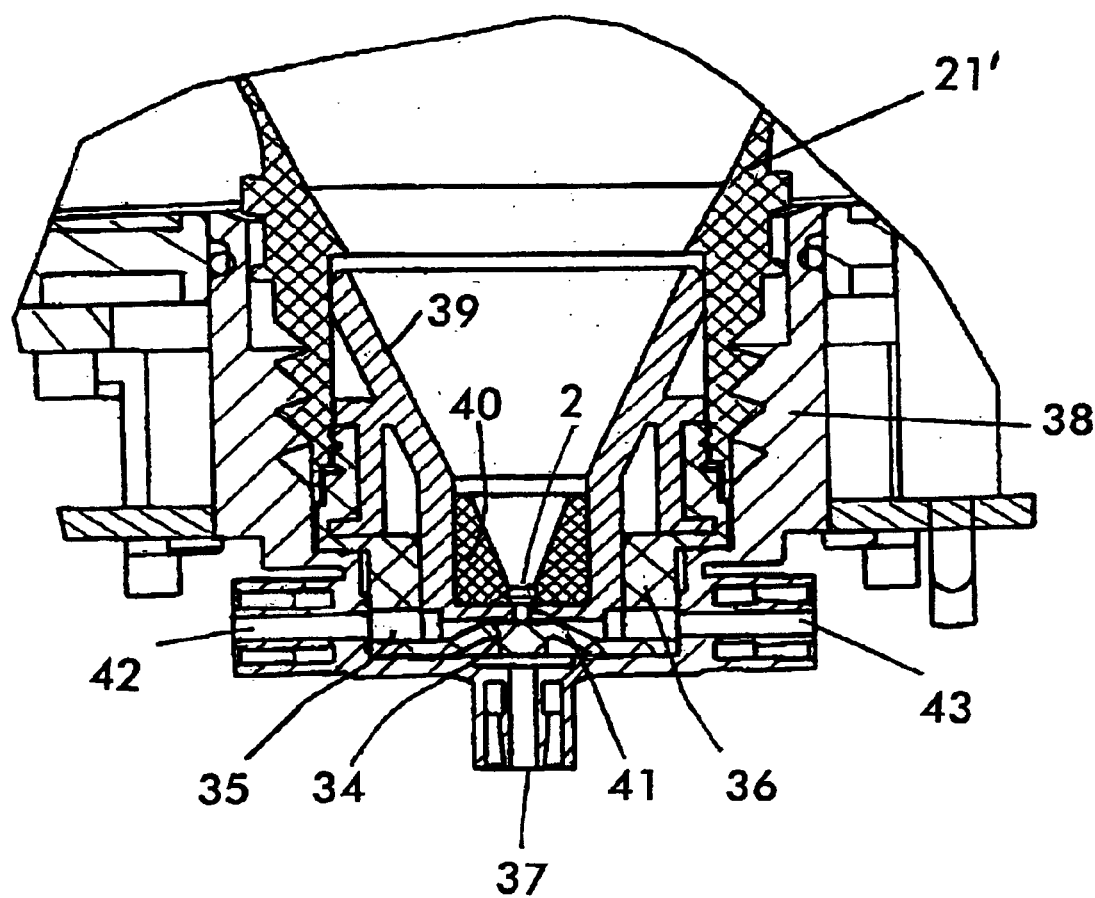
FIG. 6 is a sectional view of a fourth embodiment of the discharge valve incorporating also a pneumatic drive as in the case of the valve arrangement of FIG. 5 but differently designed.

The embodiment which is illustrated in FIG. 6 also comprises a pneumatic driving means as in case of the embodiment of FIG. 5. The closure body of a discharge valve is provided by an undercut wall portion 34 of a passage line 35 for compressed air as integrated with a rubber-elastic body 36 as in case of the embodiment of FIG. 2. The undercut wall portion 34 forms a diaphragm which is arranged for directly closing the discharge opening 2 of the powder reservoir under the action of pressure pulses which are supplied via a connecting bore 37 of a screw member 38 which is screw-connected with a neck portion 21' of the powder reservoir. It is of course to be understood that the diaphragm which as a closure body of the discharge valve is formed by the undercut wall portion 34 of the passage line 35 will be alternately moved into an opening position by a release of the pressure pulse which is supplied via the connecting bore 37 from the pneumatic driving means which will be operated with the same pulse frequency as in case of the embodiment of FIG. 2. The discharge opening 2 of the powder reservoir is formed by an insert member 39 which is held on the neck portion 21' by the member 38 whereby a rubber bushing 40 is further inserted into the discharge portion of the insert body 39 accommodating both the discharge opening 2 which is aligned with a passage opening 41 that connects to the mixing chamber. The mixing chamber is formed by an intermediate portion of the passage line for compressed air which has opposite connecting ends 42 and 43 with the supply line 4 of the pressure source 5 and the connecting line 12 with the associated handpiece 13 of the dental abrasive blasting apparatus.

We claim:

1. A powder reservoir for a dental abrasive blasting apparatus which is connected with a handpiece having a nozzle arrangement at a tip portion for discharging a jet stream of a mixture of compressed air and abrasive powder particles which is supplied from a mixing chamber that is arranged below a discharge opening of the powder reservoir, comprising:
   a discharge valve having a closure body which is biased towards a closing position of the discharge opening of the powder reservoir for blocking discharge of powder particles into the mixing chamber, and
   driving means associated with the closure body of the discharge valve for moving the closure body into a pulsed opening position alternately with respect to its closing position in which the powder particles are discharged from the powder reservoir for being mixed with a stream of compressed air which is passed through the mixing chamber at a position underneath of the discharge opening whereby a pulse frequency of the driving means which is associated with the closure body of the discharge valve is chosen such as to determine a desired dosage for the mixture of the powder particles with the compressed air,
   wherein the pulse frequency of the driving means is controlled in a range between 0.5 and 100 Hz at pulse width between 0 and 100%.

2. The powder reservoir according to claim 1, wherein the closure body of the discharge valve is formed as a substantially needle-shaped closure member which projects towards the discharge opening of the powder reservoir for closing and opening the same when being relatively moved.

3. The powder reservoir according to claim 2, wherein the needle-shaped closure member is arranged on a diaphragm serving as a pressure multiplier.

4. The powder reservoir according to claim 1, wherein the closure body of the discharge valve is formed with a disk-shaped diaphragm.

5. The powder reservoir according to claim 1, wherein the driving means associated with the closure body of the discharge valve comprises a lifting magnet of an electromagnetic drive.

6. The powder reservoir according to claim 1, wherein the driving means associated with the closure body of the discharge valve comprises a pneumatic drive.

7. The powder reservoir according to claim 6, wherein the pneumatic drive comprises a piston which is driveably connected to the closure body of the discharge valve.

8. The powder reservoir according to claim 6, wherein the closure body of the discharge valve is arranged for being driven intermittently by pressure pulses of the pneumatic drive.

9. The powder reservoir according to claim 1, wherein the mixing chamber is provided by an attach unit which is arranged for being connected to the powder reservoir together with the discharge valve and its driving means.

10. The powder reservoir according to claim 9, wherein the attach unit has a screwtype connection with a lower neck portion of the powder reservoir.

11. The powder reservoir according to claim 1, wherein the closure body of the discharge valve is biased by a compression spring towards its closing position on the discharge opening of the powder reservoir.

12. The powder reservoir according to claim 1, wherein the closure body of the discharge valve is biased by a pneumatic pressure compensation towards its closing position on the discharge opening of the powder reservoir whereby the pneumatic pressure compensation is obtained by a branch line of the stream of compressed air which in the mixing chamber is passed over the upper surface of the closure body for its mixture with the powder particles, the branch line connecting to a pressure compensation chamber which is provided beneath the closure body of the discharge valve.

13. The fluid reservoir according to claim 1, wherein the discharge valve comprises a rubber-elastic member which has a primary cup-shaped chamber for a slip-on fixation of the rubber-elastic member on a lower neck portion of the powder reservoir, and a secondary chamber which is interconnected with the primary chamber via a passage opening that is aligned with the discharge opening of the powder reservoir, the secondary chamber forming the mixing chamber and being provided with a unitary passage line for the compressed air whereby an undercut wall portion of the passage line for the compressed air is biased as a closure body of the discharge valve towards a closing position of the passage opening.

14. The powder reservoir according to claim 13, wherein the undercut wall portion of the unitary passage line for compressed air of the mixing chamber is arranged for forming by itself a diaphragm as a closure body of the discharge valve.

15. The powder reservoir according to claim 13, wherein the undercut wall portion of the unitary passage line for compressed air of the mixture chamber is formed with an integrated needle-shaped projection as a closure body of the discharge valve and projecting via the oppositely arranged passage opening into the discharge opening of the powder reservoir.

16. The powder reservoir according to claim 13, wherein the branch line connects to the undercut wall portion of the unitary passage line for compressed air of the mixing chamber.

17. The powder reservoir according to claim 13, wherein the intermittently activated pressure pulses are arranged for acting on the undercut wall portion of the unitary passage line for compressed air of the mixing chamber.

18. A powder reservoir for a dental abrasive blasting apparatus which is connected with a handpiece having a nozzle arrangement at a tip portion for discharging a jet stream of a mixture of compressed air and abrasive powder particles which is supplied from a mixing chamber that is arranged below a discharge opening of the powder reservoir, comprising:

a discharge valve having a closure body which is biased towards a closing position of the discharge opening of the powder reservoir for blocking discharge of powder particles into the mixing chamber, and driving means associated with the closure body of the discharge valve for moving the closure body with a pulse frequency into a pulsed opening position alternately with respect to its closing position so that the powder particles are discharged from the powder reservoir in a pulsed sequence for being mixed with a stream of compressed air which is passed through the mixing chamber at a position underneath of the discharge opening, said closure body of the discharge valve being moved with said pulse frequency so as to determine a desired dosage for the mixture of the powder particles with the compressed air while said air is passed through said mixing chamber.

19. A powder reservoir according to claim 18, wherein the pulse frequency of the driving means is controlled in a range between 0.5 and 100 Hz at pulse width between 0 and 100%.

* * * * *